(12) United States Patent
Scudere

(10) Patent No.: US 6,976,971 B2
(45) Date of Patent: Dec. 20, 2005

(54) ARM SLING

(76) Inventor: Carol Scudere, 5259 Cleveland Ave., Columbus, OH (US) 43231

(*) Notice: Subject to any disclaimer, the term of this patent is extended or adjusted under 35 U.S.C. 154(b) by 2 days.

(21) Appl. No.: 10/376,909

(22) Filed: Feb. 27, 2003

(65) Prior Publication Data
US 2003/0163069 A1 Aug. 28, 2003

Related U.S. Application Data

(60) Provisional application No. 60/360,125, filed on Feb. 27, 2002.

(51) Int. Cl.$^7$ ............................................. A61F 5/00
(52) U.S. Cl. ......................................... 602/4; 602/5
(58) Field of Search .... 602/4, 5, 20–23; 126/877–879, 126/882

(56) References Cited

U.S. PATENT DOCUMENTS

| | | | |
|---|---|---|---|
| 2,594,809 A | 4/1952 | Sanders | 122/94 |
| 3,433,221 A | 3/1969 | Kendall et al. | 128/94 |
| 4,232,664 A * | 11/1980 | Blatt | 602/4 |
| 4,285,337 A * | 8/1981 | Cosentino | 602/4 |
| 4,372,301 A | 2/1983 | Hubbard et al. | 128/94 |
| 4,550,724 A * | 11/1985 | Berrehail | 128/874 |
| 4,572,172 A | 2/1986 | Williams | 128/94 |
| 4,622,961 A | 11/1986 | Christensen | 128/94 |
| 4,759,353 A * | 7/1988 | Melendez et al. | 602/4 |
| 4,915,097 A * | 4/1990 | West | 128/77 |
| 5,334,132 A | 8/1994 | Burkhead | 602/4 |
| 5,772,617 A * | 6/1998 | Lay | 602/4 |
| 6,770,044 B1 * | 8/2004 | Joslin | 602/4 |

* cited by examiner

Primary Examiner—Michael A. Brown
(74) Attorney, Agent, or Firm—Mueller and Smith, LPA

(57) ABSTRACT

An arm sling that allows for parts of a patient's limb to extend from a portion of the sling for either exercise or use of the limb or hand, while the remainder of the limb or shoulder is supported by the sling without increasing pressure on the patient's neck. A support strap portion having a connector is attached to a body portion having wrist, elbow and forearm portions. The body portion also has front and rear panels. An opening in the rear panel allows the wearer's forearm, wrist and hand to pass through while the elbow and shoulder continue to be supported by the sling. In alternate embodiments the support strap may be of variable length, and may have a slidable pad surrounding the support strap.

10 Claims, 2 Drawing Sheets

ARM SLING

This application claims the benefit of U.S. Provisional Application No. 60/360,125, filed Feb. 27, 2002.

FIELD OF THE INVENTION

The embodiments are directed towards an arm sling having an opening in a rear panel that allows a portion of a user's arm to pass out of the sling, while still supporting major joints of the arm and shoulder.

BACKGROUND

An important part of medical treatment for an arm or shoulder injury consists of supporting the arm, which is usually accomplished by means of an arm sling. Injuries may comprise sprains, fractures, ligament damage to arm joints, a torn rotator cuff or the like. After diagnosis and repair of the injured area, the injury may be partially treated by supporting a forearm in a slightly elevated and retracted position with an arm sling. Thus, arm slings are provided to both support the arm and limit movement of the arm and shoulder during the healing process. The restraining effect of the arm sling promotes healing because the limb is immobilized, giving the patient's bones and tissues an opportunity to heal.

Typically, arm slings are square or rectangular sections of material folded to form a pocket for supporting an arm. A strap or other device is coupled to opposite ends of the sling and directed around a patient's neck, where the sling is suspended from the strap to support the injured limb or shoulder. Variations on this typical sling include some with waist belts, multiple straps, and padded straps for additional support or increased comfort. Although immobilizing the limb or shoulder assists in the healing process, it may also have a debilitating effect on the joints and muscles because of in activity, resulting in stiffness and loss of extension range. Many upper arm or shoulder injuries do not require the entire arm or hand to be immobilized; likewise, it is sometimes necessary to use the non-injured arm or hand while still supporting the elbow or shoulder. Unfortunately, completely removing the arm from the sling leaves the limb unsupported, making the injured area susceptible to further injury or increased pain. Extending a hand from the end of a bunched up sling provides for use of the hand, but at the expense of increased pressure on the neck from the sling's strap. In addition, arm slings available in the art also provide inadequate or uncomfortable support for short-armed or heavy patients because of the angle of the sling at rest. There is a need for an arm sling that provides the necessary support and restraint while allowing the wearer the use of their arm or hand.

SUMMARY

The present invention is an arm sling that allows for parts of a patient's limb to extend from a portion of the sling for either exercise or use of the limb or hand, while the remainder of the limb or shoulder is supported by the sling without increasing pressure on the patient's neck. A support strap portion having a connector is attached to a body portion having wrist, elbow and forearm portions. The body portion also has front and rear panels. An opening in the rear panel allows the wearer's forearm, wrist and hand to pass through while the elbow and shoulder continue to be supported by the sling.

BRIEF DESCRIPTION OF THE DRAWINGS

Further features of the present invention will become apparent to those skilled in the art to which the embodiments relate from reading the following specification and claims, with reference to the accompanying drawings, in which:

DESCRIPTION OF THE PREFERRED EMBODIMENTS(S)

Figure 1:
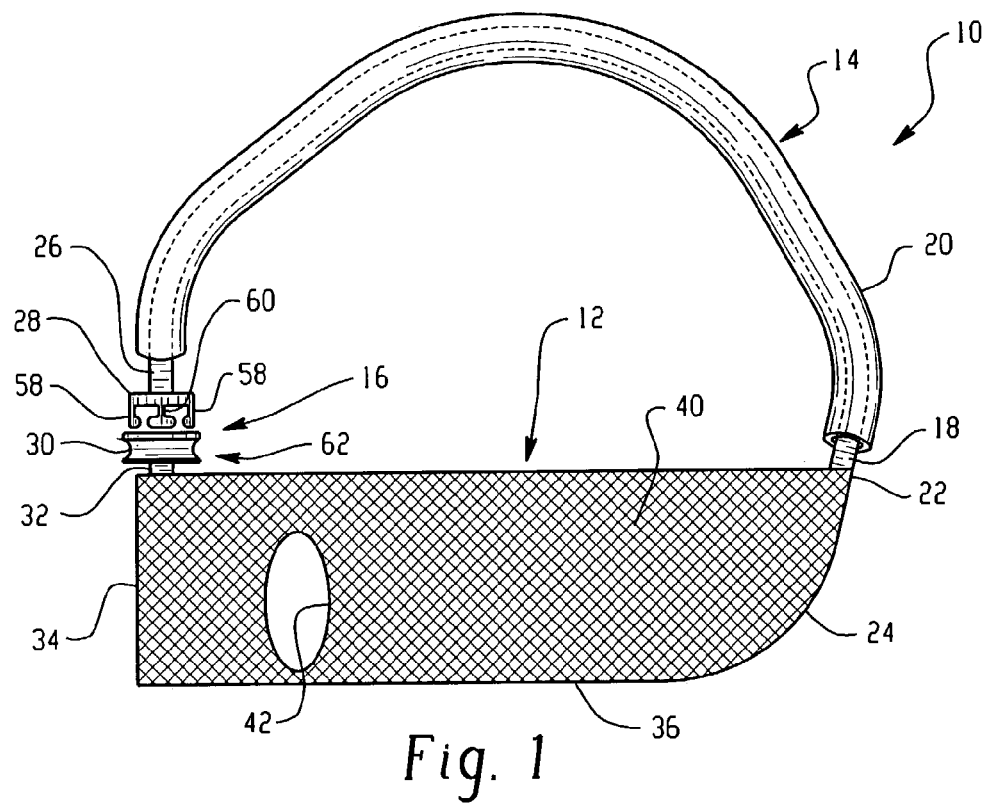
FIG. 1 is a side view of an inside surface of an arm sling according to an embodiment of the present invention.

As seen in FIGS. 1–4, an arm sling 10 according to an embodiment of the present invention comprises a body portion 12, a support strap portion 14, and a connecting portion 16. The support strap portion 14 comprises a support strap 18 that may be substantially surrounded by a slidable pad 20 running substantially the entire length of the support strap portion 14. The slidable pad 20 may be permanently made part of support strap portion 14, or may be separately removable. The pad 20 may be made from any suitable materials, such as lamb's wool, fabric, leather, suede, synthetics and foam. Various levels of padding may be used for the pad 20, and the pad may be flat, oval or tubular in shape. A first end 22 of the support strap portion 14 is coupled to an elbow portion 24 of the body portion 12. A second end 26 of the support strap portion 14 is coupled to a first connecting device 28 of the connecting portion 16. A second connecting device 30 may be coupled via a second strap portion 32 to a wrist portion 34 of the body portion 12; alternatively, the second connecting device 30 may be directly coupled to body portion 12. Positioned between the wrist portion 34 and the elbow portion 24 of the body portion 12 is a forearm portion 36. The body portion 12 may be made from any suitable material. Examples include, but are not limited to, fabrics, padded fabrics, and meshes.

Figure 2:
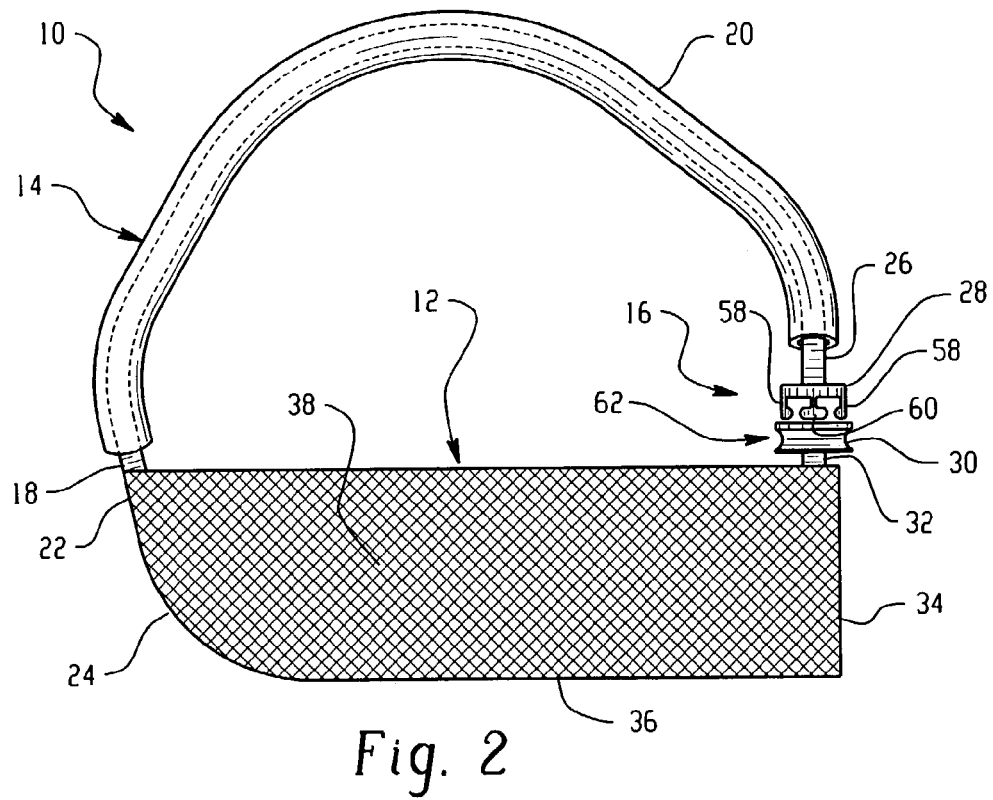
FIG. 2 is a side view of an outside surface of an arm sling according to an embodiment of the present invention.
Figure 3:
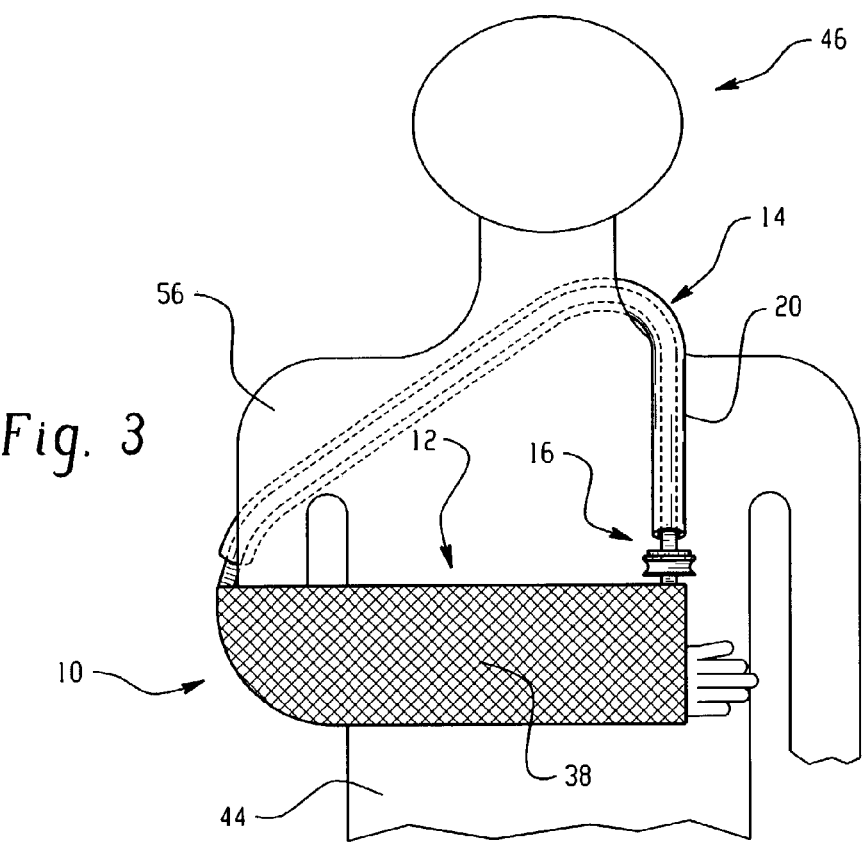
FIG. 3 is a view of a person wearing an arm sling according to an embodiment of the present invention.

Turning now to FIGS. 2–3, with continuing reference to FIG. 1, the body portion 12 further comprises a front panel 38 opposite to a back or rear panel 40 comprising an opening 42. The front panel 38 may be away from a torso 44 (FIG. 3) of a user 46, while the rear panel 40 may be touching the torso 44 of a user 46.

Figure 4:
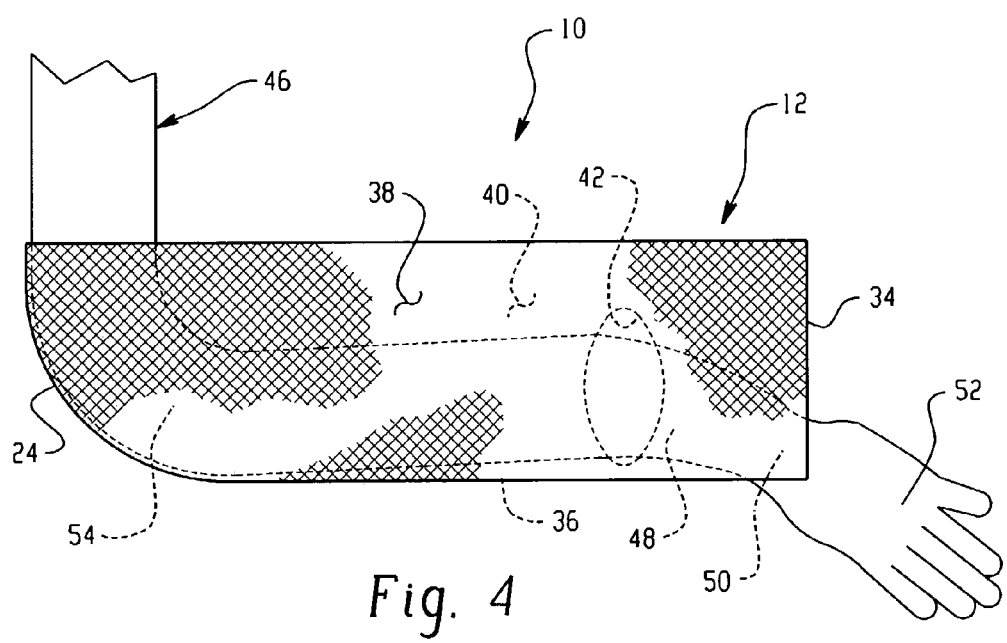
FIG. 4 is an expanded view of a person wearing an arm sling, showing the arm passing through an opening in an inside surface of the sling according to an embodiment of the present invention.

Turning now to FIG. 4, with continuing reference to FIG. 3, when the sling 10 is worn by the user 46, a forearm 48, wrist 50, and hand 52, or parts thereof, may pass through the opening 42, while an elbow 54 and shoulder 56 (FIG. 3) may continue to be supported by the sling 10. Thus, the user 46 may extend the desired parts of the forearm 48, wrist 50, and hand 52 from the sling 10 in order to exercise a limb, perform physical therapy on the limb, or to perform everyday household or business related tasks, while still fully supporting the elbow 54 and shoulder 56 with the sling 10. Use of the sling 10 may reduce atrophy and stiffness during rehabilitation and healing of a limb, and provide for utility of the limb while also maintaining the proper support at all times for the major joints of the limb.

With reference again to FIGS. 1 and 2, an embodiment of the connecting portion 16 comprises a male portion 28 and a female portion 30 to form a locking buckle. In the embodiments shown, the male portion 28 has two side extensions 58 and middle extension 60, which are received in the complementary female portion receiving section 62. It will be readily recognized by those skilled in the art that the male portion 28 and female portion 30 may be swapped, if desired, without affecting the function of the connecting portion 16. In alternative embodiments, any connecting device known in the art may be used, such as snaps, clips, hooks, loops, VELCRO®, buttons, buckles, clasps, pins, and ties.

The body portion 12 of sling 10 may be constructed to a longer length than those generally available in the art. A longer sling body portion 12 in relation to the length of a patient's arm both accommodates the comfort of those patients with shorter arms or who may be particularly large. In alternate embodiments, length of the support strap portion 14 may be varied by adjusting the length of the support strap 18. Example length adjusting means include, but are not limited to, VELCRO®, buttons, sliding buckles and rings.

The various embodiments have been described in detail with respect to specific embodiments thereof, but it will be apparent that numerous variations and modifications are possible without departing from the spirit and scope of the embodiments as defined by the following claims.

What is claimed is:

1. A method for performing tasks with the hand or wrist of a user's arm which is supported in an arm sling, comprising the steps of:
   (a) providing an arm sling comprising
      (i) a body portion having a generally horizontal portion extending from the elbow to at least the wrist of the user's arm and having a back panel, the back panel having an opening extending there through substantially opposite the elbow to accommodate lateral movement of one or more of the hand or the wrist when the user's arm is inserted in the body portion; and
      (ii) a support strap connected to the body portion and adapted to go around the neck of the user for supporting the body portion;
   (b) inserting the user's arm through the opening in the back panel of the body portion of the arm sling;
   (c) securing the support strap about the neck of the user; and
   (d) when the user desires to perform a task, laterally moving one or more of the hand or the wrist through the opening, whereby the user can perform a task with the extended one or more of the hand or wrist.

2. The method of claim 1, wherein the arm sling provided in step (a) further comprises a slidable pad surrounding the support strap substantially along its length.

3. The method of claim 2, wherein the slidable pad is removable from the support strap.

4. The method of claim 2, wherein the slidable pad is made from lamb's wool.

5. The method of claim 1, wherein the support strap of step (a) further includes adjusting means for varying the length of the support strap.

6. The method of claim 1, wherein the body portion of step (a) is made of fabric.

7. The method of claim 1, wherein the body portion of step (a) is made of mesh material.

8. The method of claim 1, wherein:
   the support strap further comprises first and second ends, the first end of the support strap being coupled to the body portion near the elbow portion;
   first and second connecting devices comprising complementary connecting sections that couple to releasably secure the first and second connecting devices, a first connecting device being coupled to the second end of the support strap; and
   the second connecting device coupled to the body portion near the wrist portion.

9. The method of claim 8, wherein the first and second connecting devices comprise male and female portions, respectively, of a locking buckle.

10. The method of claim 1, wherein the body portion of step (a) extends at least to the hand.

* * * * *